(12) United States Patent
Kirkpatrick (10) Patent No.: US 8,465,454 B2
(45) Date of Patent: Jun. 18, 2013

(54) MATRIX INFUSION PUMP AND DISPOSABLE SET

(75) Inventor: Gregg Kirkpatrick, San Diego, CA (US)

(73) Assignee: CareFusion 303, Inc., San Diego, CA (US)

( * ) Notice: Subject to any disclaimer, the term of this patent is extended or adjusted under 35 U.S.C. 154(b) by 315 days.

(21) Appl. No.: 12/842,856

(22) Filed: Jul. 23, 2010

(65) Prior Publication Data

US 2012/0022494 A1 Jan. 26, 2012

(51) Int. Cl.
*A61M 37/00* (2006.01)
*A61M 1/00* (2006.01)
*F04B 43/08* (2006.01)
*F04B 43/12* (2006.01)
*F04B 43/06* (2006.01)

(52) U.S. Cl.
USPC .................... 604/132; 604/151; 417/477.2

(58) Field of Classification Search
USPC ................ 604/151–155, 131–133; 417/477.2
See application file for complete search history.

(56) References Cited

U.S. PATENT DOCUMENTS

| 4,657,490 | A | 4/1987 | Abbott |
| 5,429,485 | A | 7/1995 | Dodge |
| 5,695,473 | A | 12/1997 | Olsen |
| 5,718,569 | A | 2/1998 | Holst |
| 7,744,554 | B2 * | 6/2010 | Howard ....................... 604/6.11 |
| 2006/0211989 | A1 * | 9/2006 | Rhinehart et al. ............ 604/151 |

* cited by examiner

*Primary Examiner* — Nicholas D Lucchesi
*Assistant Examiner* — Rebecca E Eisenberg
(74) *Attorney, Agent, or Firm* — McDermott Will & Emery LLP (57) ABSTRACT

A matrix infusion cassette for use with an intravenous (IV) pump is disclosed. The matrix infusion cassette includes a body configured to attach to the IV pump, the body having one or more inlet ports, an outlet port, and a plurality of pumping chambers, and a plurality of fluid conduits connecting the inlet ports to at least one pumping chamber, interconnecting the pumping chambers, and connecting at least one pumping chamber to the outlet port.

14 Claims, 12 Drawing Sheets

MATRIX INFUSION PUMP AND DISPOSABLE SET

FIELD

The present disclosure generally relates to administration of medical fluid by infusion and, in particular, relates to a system and method of pumping infusion fluids.

BACKGROUND

Infusion pumps have become commonplace within the healthcare world as a way to precisely administer intravenous (IV) fluids. Use of a pump in place of a simple roller clamp with an elevated fluid container to control the flow of the IV fluid allows more accurate and consistent control of the rate of delivery of the fluid to the patient.

One of the challenges facing infusion pump designers is providing accurate delivery at very low flow rates while retaining a maximum flow capability that is sufficient to meet the needs of most patients. Volumetric pumps are used to administer fluids for hydration or nutrition and can deliver up to 2 liters of fluid from sources such as a bag or bottle and are generally suitable to deliver at flow rates of 5 to 2,000 ml/hr. Syringe pumps are used for accurate administration of fluids and are generally suitable to deliver at flow rates of 0.1 to 100 ml/hr but are typically limited to a syringe volume of approximately 100 ml of fluid.

SUMMARY

For some or all of the reasons listed above, it is desirable to provide the ability to control the flow of intravenous fluids over a wide range of flow rates while providing precise and near-continuous delivery at the lowest flow rates.

A matrix infusion cassette for use with an intravenous (IV) pump is disclosed. The matrix infusion cassette comprises a body configured to attach to the IV pump, the body having one or more inlet ports, an outlet port, and a plurality of pumping chambers, and a plurality of fluid conduits connecting the inlet ports to at least one pumping chamber, interconnecting the pumping chambers, and connecting at least one pumping chamber to the outlet port.

A matrix infusion pump configured to actuate a matrix infusion cassette having a plurality of pumping chambers and a plurality of valves is disclosed. The matrix infusion pump comprises a housing configured to attach to the matrix infusion cassette, a plurality of pumping actuators attached to the housing and configured to actuate the pumping chambers, a memory attached to the housing and configured to store instructions, and a processor attached to the housing and coupled to the memory and the actuators. The processor is configured to retrieve the instructions from the memory and to cause one or more of the pumping actuators to actuate the pumping chambers according to the instructions.

A method of providing an accurate rate of delivery of medical fluid over a wide range of flow rates is disclosed. The method comprises the steps of selecting an IV set having a matrix infusion cassette with a range of flow rates that includes a first flow rate for delivery of medical fluid to a patient, connecting and configuring the IV set for the patient with a matrix infusion pump and a source of medical fluid, and configuring the matrix infusion pump to deliver the medical fluid at the first flow rate.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

The disclosed embodiments of a matrix infusion cassette, used in conjunction with an IV pump configured to actuate the matrix infusion cassette, provide a wide range of flow rates with precise control of the flow rate at the low end of the range. Certain embodiments of the matrix infusion cassette may be configured to provide independent control of the flow rate of multiple fluids.

In the following detailed description, numerous specific details are set forth to provide a full understanding of the present disclosure. It will be apparent, however, to one ordinarily skilled in the art that embodiments of the present disclosure may be practiced without some of the specific details. In other instances, well-known structures and techniques have not been shown in detail so as not to obscure the disclosure.

Figure 1A:
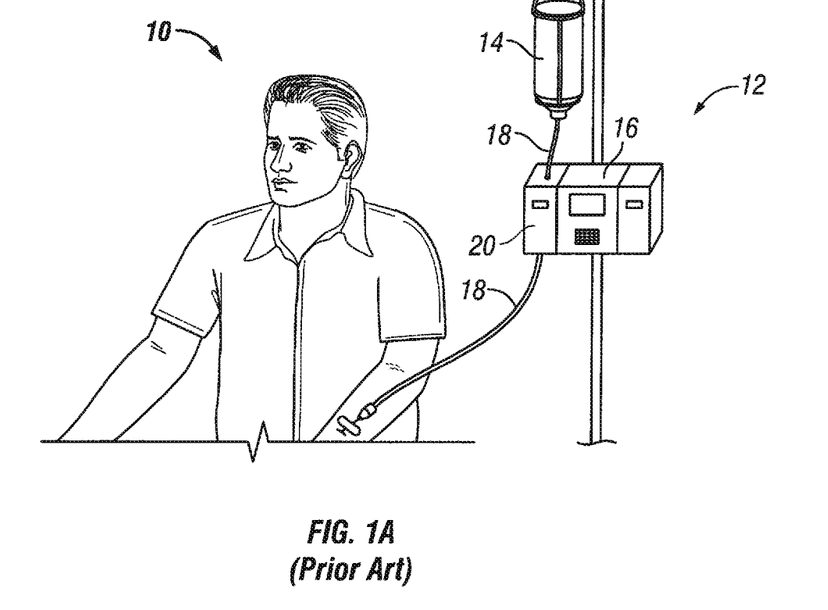
FIG. 1A is a diagram of an example embodiment of a patient receiving medical fluid through an intravenous line using an infusion pump.

FIG. 1A is a diagram of an example embodiment of a patient 10 receiving medical fluid from, in this example, a flexible bag 14 through an intravenous set 18 using an infusion pump 12. IV set 18 includes the complete set of lines and fitting connecting the flexible bag 14 to the patient 10. Pump 12 includes a controller 16 and a pumping module 20. In some IV systems, line 18 passes through pumping module 20 and then to the patient 10.

Figure 1B:
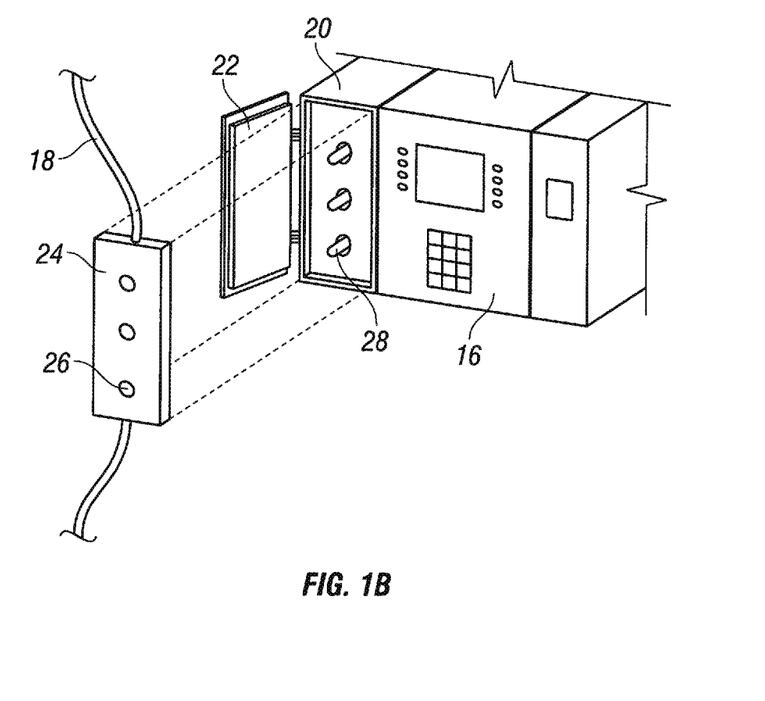
FIG. 1B illustrates attachment of a matrix infusion cassette to the infusion pump of FIG. 1A according to certain embodiments of the present disclosure.

FIG. 1B illustrates attachment of a matrix infusion cassette to the infusion pump of FIG. 1A according to certain embodiments of the present disclosure. Pumping module 20 has a door 22 that, in this illustration, is in an open position. The intravenous line 18 has a matrix infusion cassette 24 incorporated into the fluid path. The matrix infusion cassette 24 has, in this example, three pumping chambers 26, although more or fewer pumping chambers are provided in alternate embodiments. The pumping module 20 includes, in this example, three pumping actuators 28. The matrix infusion cassette 24 is placed within the pumping module 20 as indicated by the broken lines and the door closed for use, whereupon the pumping chambers 26 are co-located with the pumping actuators 28. A matrix infusion cassette 24 may be provided as a separate device having connectors, such as male or female Luer fittings, or may be provided with lengths of IV tubing pre-attached to one or more of an inlet or outlet of matrix infusion cassette 24.

Figure 2A:
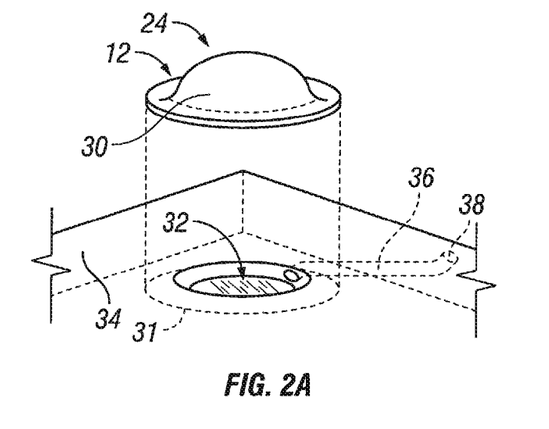
FIGS. 2A-2D discloses alternate embodiments of the pumping chambers of a matrix infusion cassette according to certain embodiments of the present disclosure.
Figure 2B:
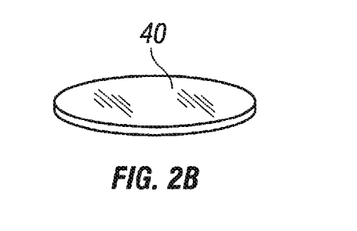
Figure 2C:
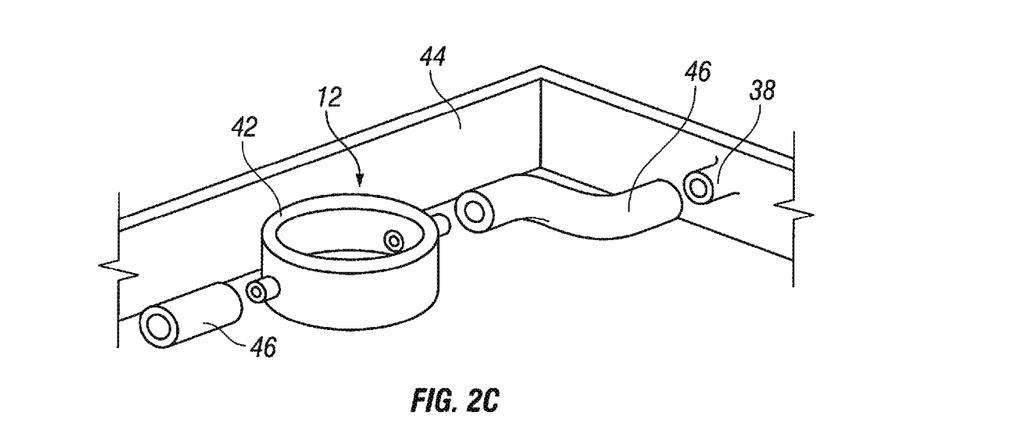
Figure 2D:
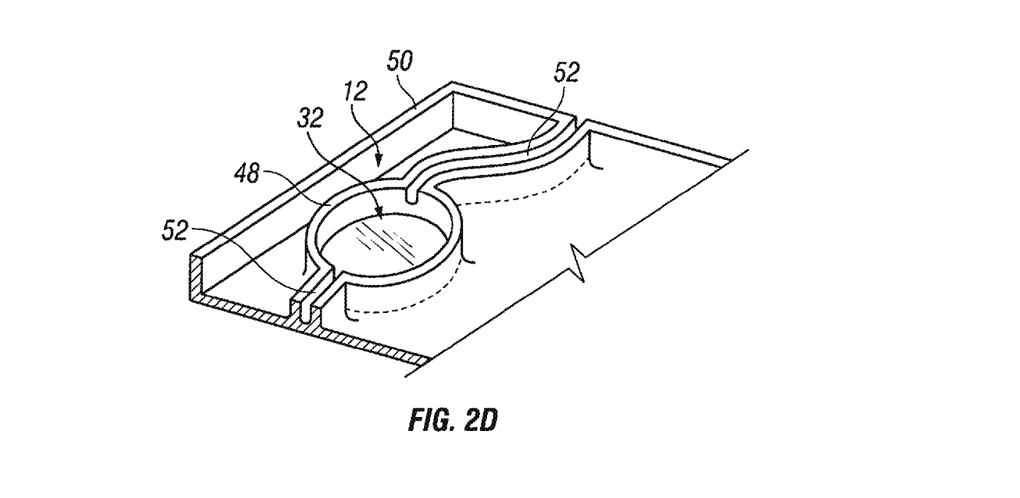

FIGS. 2A-2D disclose alternate embodiments of the pumping chambers of a matrix infusion cassette 24 according to certain embodiments of the present disclosure. FIG. 2A shows an exploded view of the corner of a matrix infusion cassette 24 and one pumping chamber 12. A flexible wall 30 covers the opening of a chamber 32 formed in the body 34 of matrix infusion cassette 24, the flexible wall 30 being sealed to the body 34 in the area indicated by the broken lines 31. A fluid conduit 36 is formed in the body 34 and connects the chamber 32 to, in this example, an inlet 38. Similar fluid conduits may also connect pumping chamber 12 to other pumping chambers (not shown) in the matrix infusion cassette 24 or to an outlet (not shown). FIG. 2B illustrates an alternate embodiment of a flexible wall 40 that may be used in place of the dome-shaped flexible wall 30. Additional embodiments of a flexible wall will be apparent to those of ordinary skill in the art. FIG. 2C illustrates an alternate embodiment of a pumping chamber 12 formed as a separate housing 42 that is attached to body 44. In this embodiment, the fluid conduits are distinct tubes 46 that connect the pumping chamber 12 to the inlet 38 or may interconnect this pumping chamber 12 to other pumping chambers (not shown) or to the outlet (not shown). FIG. 2D discloses a third embodiment wherein the pumping chamber 12 has been formed as a circumferential wall 48 that is molded as part of body 50 to form chamber 32. The fluid conduits are provided, in this example, by channels 52 that are also molded as part of body 50. The entire surface of body 50 may be covered with a sheet of material (not shown) that provides at least flexible portions over pumping chamber 12 as well as sealing the channels 52 to form fluid conduits.

Figure 3:
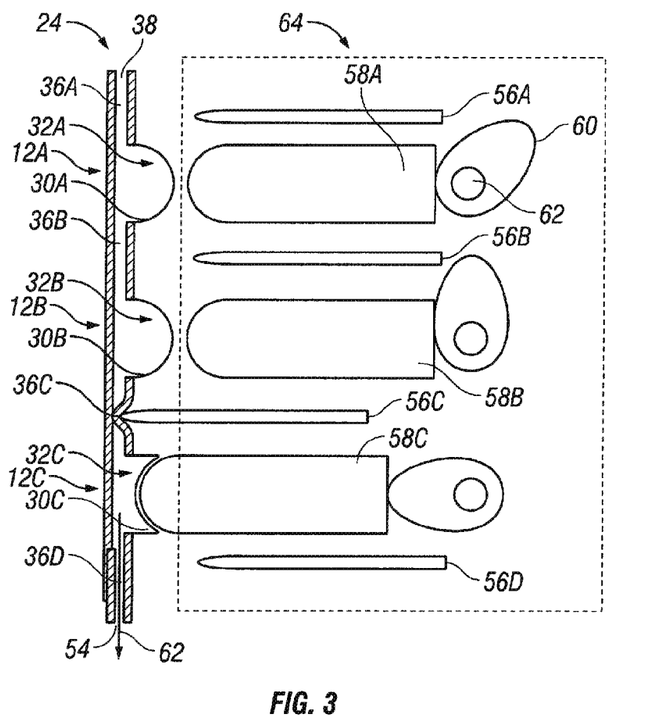
FIG. 3 is a schematic cross-section of a portion of an IV pump module and a portion of matrix infusion cassette disclosing an embodiment of a matrix infusion cassette actuation according to certain embodiments of the present disclosure.

FIG. 3 is a schematic cross-section of a portion of an IV pump module 20 and a portion of matrix infusion cassette 24 disclosing the actuation of an example embodiment of a matrix infusion cassette 24 according to certain embodiments of the present disclosure. In this example, matrix infusion cassette 24 is shown with three pumping chambers 12A-12C, each having a chamber 32A-32C, respectively, covered by a dome-shaped flexible wall 30A-30C, respectively. Pumping chamber 12a is connected to inlet 38 by fluid conduit 36A. Other fluid conduits 36B and 36C interconnect the pumping chambers 12A, 12B, and 12C and fluid conduit 36D connects pumping chamber 12C to an outlet 54. The fluid conduits 36A-36D are flexible lines that form a valve that shuts off flow through the line when the line is compressed. Other types of valves may be used, as discussed below. A portion of pump module 64, similar to the pump module 20 of FIG. 1A, is shown as enclosed by the broken line. The pumping actuators 28 of FIG. 1B comprise fingers 58A-58C that are driven by cams 60 rotating about pivots 62. Pump module 64 also includes, in this example, occluders 56A-56D. When an occluder is advanced, as shown for occluder 56C, the occluder compresses fluid conduit 36, as shown for fluid conduit 36C, blocking flow through that fluid conduit. The remaining fluid conduits remain open. In the configuration of FIG. 3, occluder 56C has blocked fluid conduit 36C and pumping actuator finger 58C has been advanced by rotation of the cam 60 behind it. The tip of pumping actuator finger 58C is compressing the flexible wall 30C forcing fluid in chamber 32C to flow through fluid conduit 36D and out through outlet 54, as indicated by arrow 62. In this configuration, a flow channel is open from inlet 38 through fluid conduit 36A into chamber 32A and through fluid conduit 36B into chamber 32B, allowing fluid to refill these chambers if they are not already full.

Alternate embodiments of valves in a matrix infusion cassette may include fluidic diodes, which allow free flow in one direction and to provide resistance to flow in the opposite direction. A fluidic diode may be a check valve having moving elements that open and close a flow path in response to pressure differentials across the valve. Other valves that are able to block fluid flow when actuated are known to those of ordinary skill in the art and may be substituted herein without departure from the scope of this invention.

Figure 4A:
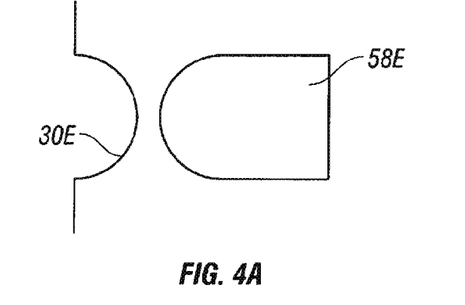
FIGS. 4A-4D illustrate demonstrate that a single size of actuator can actuate a range of volumes of pumping chambers according to certain embodiments of the present disclosure.
Figure 4B:
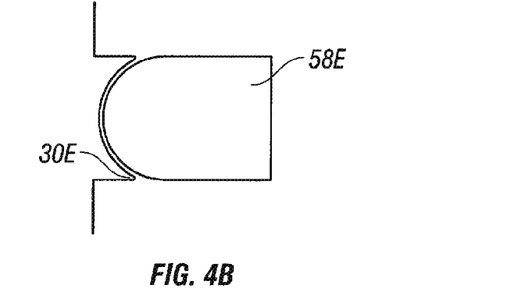
Figure 4C:
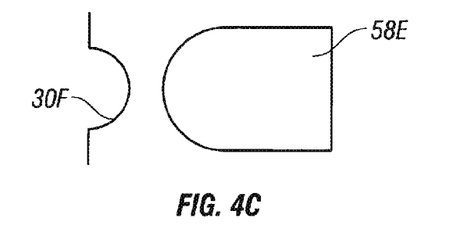
Figure 4D:
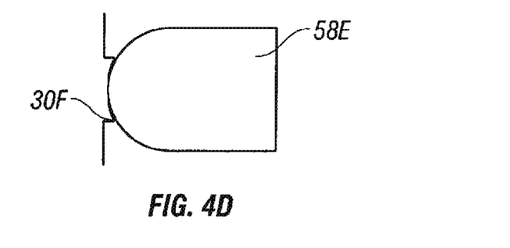

FIGS. 4A-4D illustrate demonstrate that a single size of actuator can actuate a range of volumes of pumping chambers according to certain embodiments of the present disclosure. FIG. 4A illustrates an undeformed flexible wall 30E similar to that of flexible walls 32A-C of FIG. 3 and a pumping actuator finger 58E similar to that of pumping actuator finger 58A-D of FIG. 3, wherein the diameter of pumping actuator finger 58E is close to that of flexible wall 30E. FIG. 4B illustrates the tip of pumping actuator finger 58E deforming flexible wall 30E and reducing the volume of the associated chamber. FIG. 4C illustrates a second flexible wall 30F that is half the diameter of flexible wall 30E with the same pumping actuator finger 58E as FIG. 4A. FIG. 4D shows the tip of pumping actuator finger 58E deforming flexible wall 30F. Although the size of flexible wall 30F is half the size of flexible wall 30E and of pumping actuator finger 58E, flexible wall 30F deforms in a predictable manner to pump fluid. Hence, the same pumping actuator fingers 58A-D can be employed with different types of matrix infusion cassettes.

FIGS. 5A-5J illustrate an example sequence of steps in pumping fluid using a matrix infusion cassette according to certain embodiments of the present disclosure. The configuration shown is that disclosed in FIG. 3, wherein matrix infusion cassette 24 has pumping chambers 32A-32C, inlet 38 and outlet fluid 54, and fluid conduits 36A-36D and pumping module 64 has pump actuator fingers 58A-58C and occluders 56A-56D.

Figure 5A:
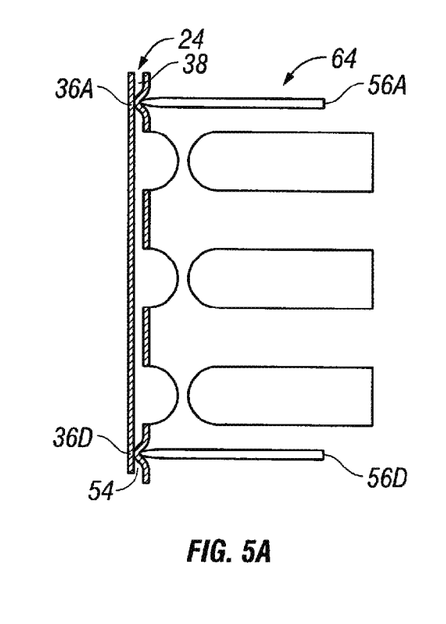
FIGS. 5A-5H and 5J illustrate an example sequence of steps in pumping fluid using a matrix infusion cassette according to certain embodiments of the present disclosure.
Figure 5B:
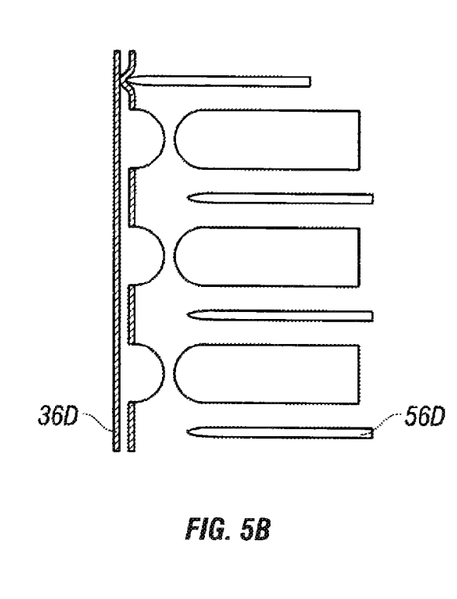
Figure 5C:
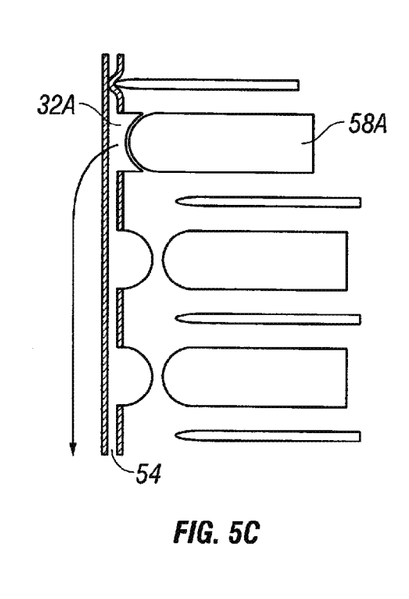
Figure 5D:
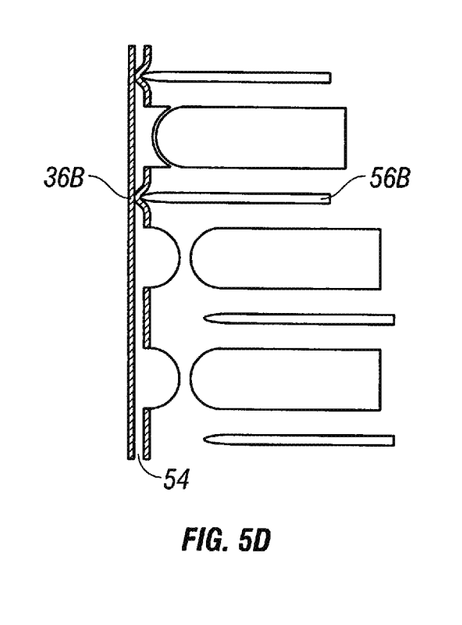
Figure 5E:
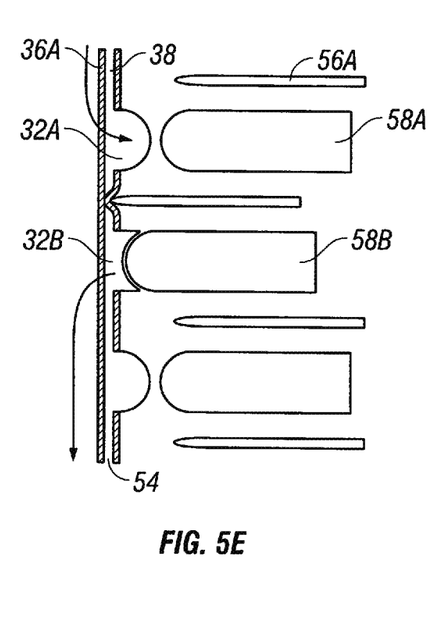
Figure 5F:
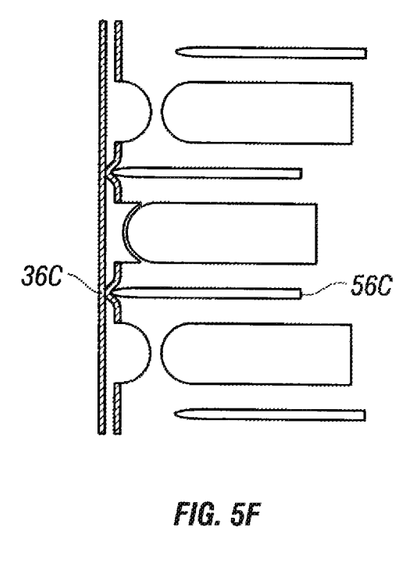
Figure 5G:
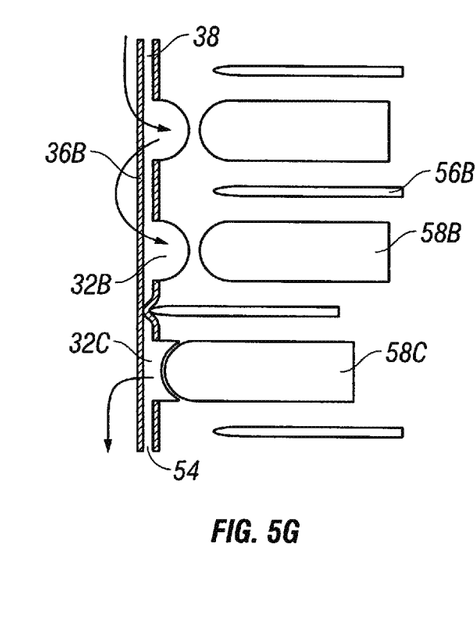
Figure 5H:
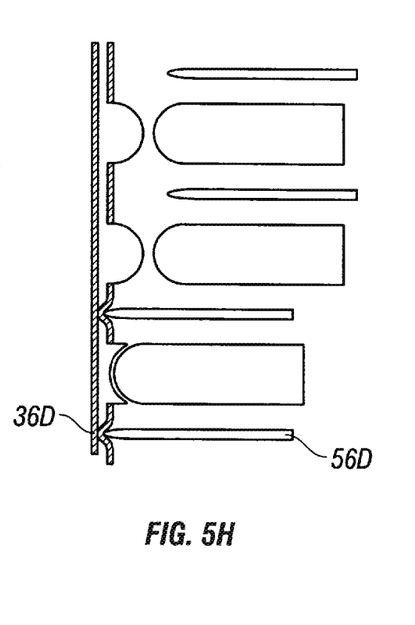
Figure 5J:
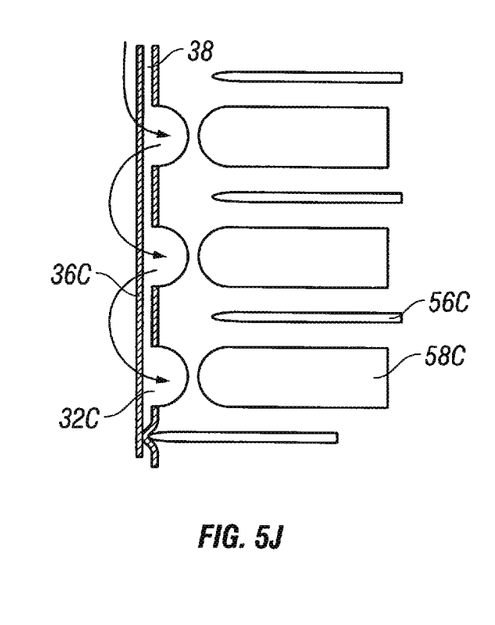

FIG. 5A depicts an initial condition of the system wherein occluders 56A and 56D are advanced, blocking fluid conduits 36A and 36D. All of the pumping actuator fingers 58A-C are retracted and the pumping chambers 32A-C and fluid conduits 36A-D are full of fluid. In FIG. 5B, occluder 56D has retracted, opening fluid conduit 36D and establishing a fluid connection from all of the pumping chambers 32A-C to outlet 54. In FIG. 5C, pumping actuator finger 58A is advancing and forcing fluid from chamber 32A to flow out of outlet 54 as indicated by the arrow. In FIG. 5D, occluder 56B has advanced, blocking flow through fluid conduit 36B and preventing any additional fluid from pumping chamber 32A from flowing out of outlet 54. In FIG. 5E, pumping actuator finger 58B is advancing, forcing fluid from pumping chamber 32B out of outlet 54 as indicated by the lower arrow. At the same time, occluder 56A and pumping actuator finger 58A have retracted and fluid is flowing in through inlet 38 into chamber 32A as indicated by the upper arrow as the chamber 32A expands. In FIG. 5F, occluder 56C has advanced, blocking flow through fluid conduit 36C. In FIG. 5G, pumping actuator finger 58C is advancing and forcing fluid from pumping chamber 32C out of outlet 54 as indicated by the lowest arrow. At the same time, occluder 56B and pumping actuator finger 58B have retracted and fluid is flowing in through inlet 38 through chamber 32A and into chamber 32B as indicated by the upper two arrows as the chamber 32B expands. In FIG. 5H, occluder 56D has advanced, blocking flow through fluid conduit 36D. Figure designator 5I has been skipped to avoid confusion of "I" and "1". In FIG. 5J, occluder 56C and pumping actuator finger 58C have retracted and fluid is flowing in through inlet 38 through chambers 32A and 32B and into chamber 32C as indicated by the three arrows as the chamber 32C expands. The next step is again shown in FIG. 5A, after occluder 56A advances and the process repeats from this point. The timing of the advancement and retraction of the various occluders and pumping actuation fingers may be adjusted to provide a more continuous flow.

Figure 6A:
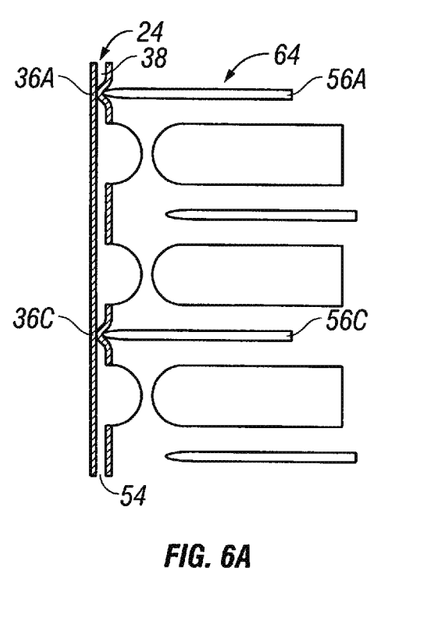
FIGS. 6A-6E illustrate an alternate sequence of steps in pumping fluid using a matrix infusion cassette according to certain embodiments of the present disclosure.
Figure 6B:
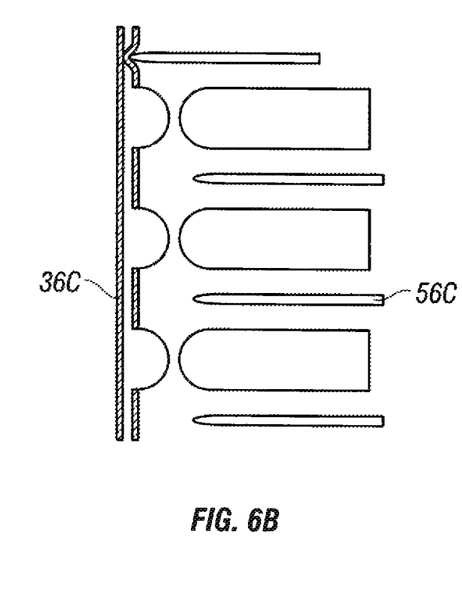
Figure 6C:
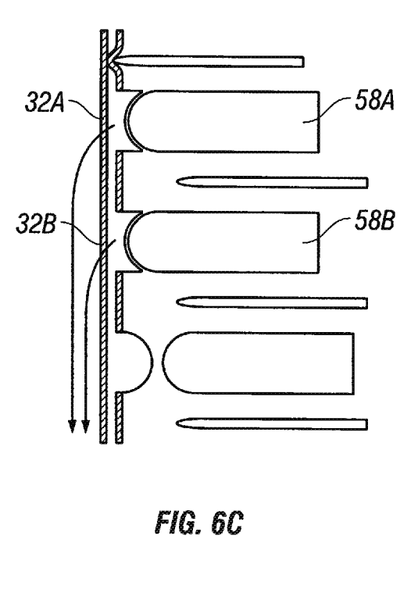
Figure 6D:
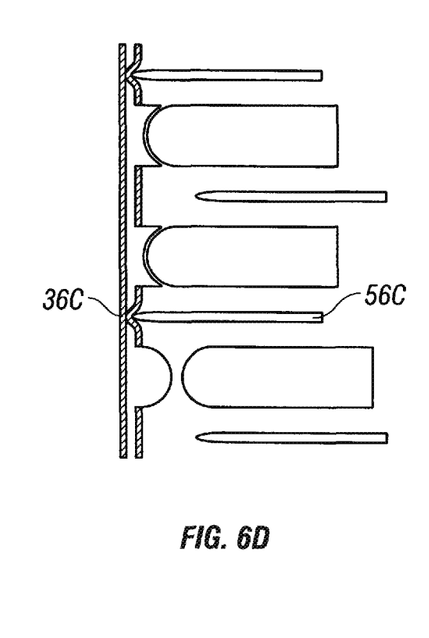
Figure 6E:
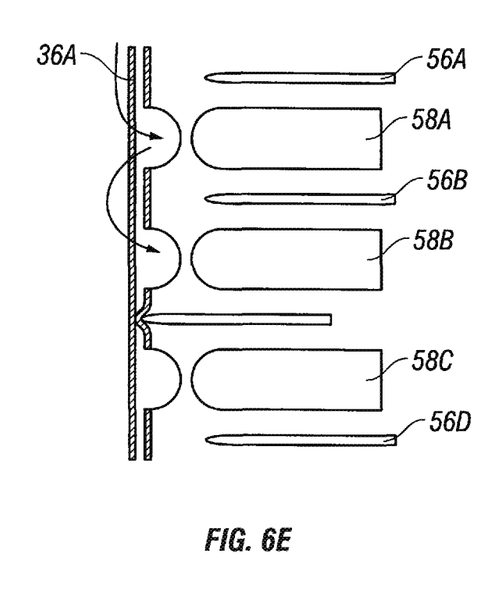

FIGS. 6A-6E illustrate an alternate sequence of steps in pumping fluid using a matrix infusion cassette according to certain embodiments of the present disclosure. The matrix infusion cassette 24 and pumping module 64 are identical to that shown in FIGS. 5A-5J. In this sequence, however, the initial position shown in FIG. 6A has occluders 56A and 56C advanced. In FIG. 6B, occluder 56C has retracted, opening a flow channel from all pumping chambers to outlet 54. In FIG. 6C, pumping actuator fingers 58A and 58B are both advancing, forcing fluid from both pumping chambers 32A and 32B to flow out through outlet 54 as indicated by the dual arrows. This flow rate may be twice the flow rate of the sequence of FIGS. 5A-5J. In FIG. 6D, occluder 56C has advanced and in FIG. 6E, occluder 56A and both pumping actuator fingers 58A and 58B have retracted, causing fluid to flow through inlet 38 into both chambers 32A and 32B as indicated by the two arrows. In this operational sequence, occluders 56B and 56D and pumping actuator finger 58C are not used, illustrating the use of a matrix infusion cassette with only a subset of the features in actual operation.

Figure 7A:
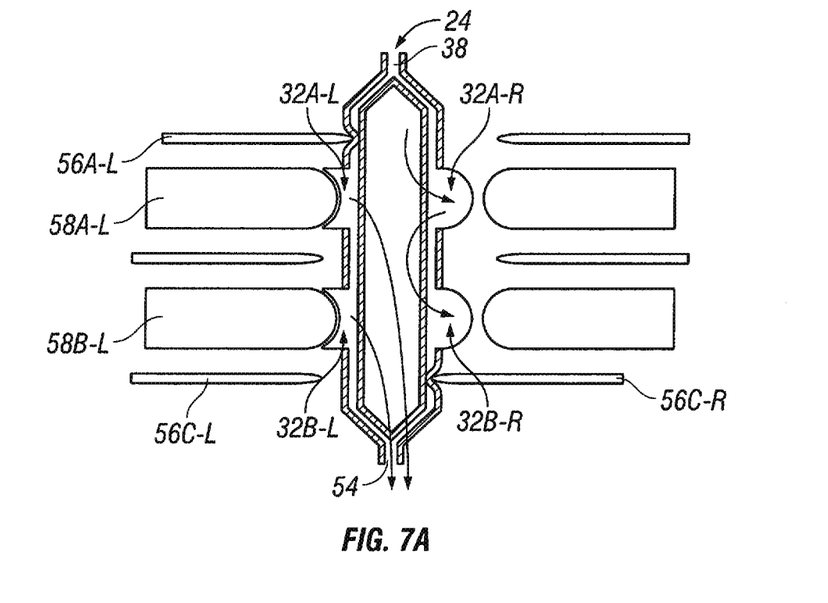
FIGS. 7A and 7B illustrate an alternate sequence of steps in pumping fluid using two parallel flow paths in a matrix infusion cassette according to certain embodiments of the present disclosure.
Figure 7B:
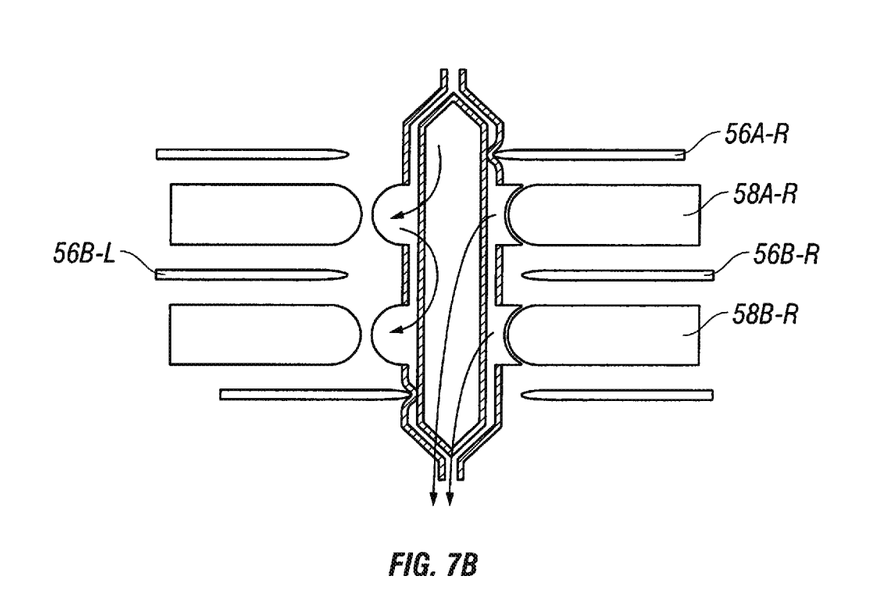

FIGS. 7A and 7B illustrate an alternate sequence of steps in pumping fluid using two parallel flow paths in a matrix infusion cassette 24 according to certain embodiments of the present disclosure. The system shown in these drawings includes a matrix infusion cassette having two parallel flow paths and the reference designators of FIGS. 6A-6E have either an "L" or an "R" appended to indicate the matching elements of the left and right flow paths. Only two pumping actuator fingers and three occluders have been shown to simplify the illustration. Similarly, some of the intermediate steps analogous to FIGS. 6B and 6D have been omitted from this sequence.

In FIG. 7A, occluder 56A-L is advanced while occluder 56C-L is retracted, pumping actuator fingers 58A-L and 58B-L are advancing, and fluid is flowing from both chambers 32A-L and 32B-L on the left flow path out through outlet 54 as indicated by the left pair of arrows. On the right side, occluder 56C-R is advanced and occluder 56A-R is retracted and both pumping actuator fingers 58A-R and 58B-R are retracted, allowing fluid to flow through inlet 38 and to fill both right-side pumping chambers 32A-R and 32B-R as indicated by the two right arrows.

In FIG. 7B, occluder 56C-L has advanced, shutting off flow through outlet 54, and occluder 56A-L and pumping actuator fingers 58A-L and 58C-L have retracted, allowing fluid to flow through inlet 38 and refill the left-side pumping chambers 32A-L and 32B-L as indicated by the two left arrows. At the same time on the right side, occluder 56A-R has advanced, shutting off the flow through inlet 38, and occluder 56C-R has retracted and pumping actuator fingers 58A-R and 58B-R are advancing, forcing fluid from the pumping chambers 32A-R and 32B-R to flow through outlet 54 as indicated by the pair of arrows on the right. It can be seen that, with proper timing of the motion of the occluders and pumping actuator fingers, near-continuous flow may be achieved at the same peak flow rate as the system of FIG. 6A-6E.

Figure 8A:
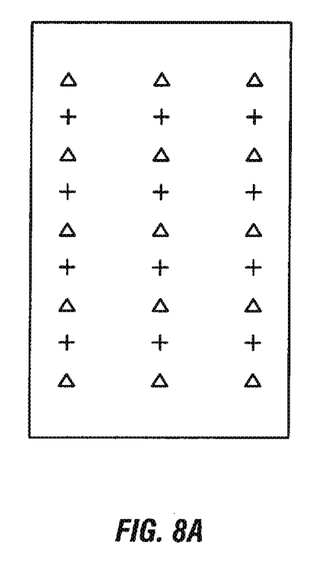
FIGS. 8A-8H and 8J discloses alternate constructions of a matrix infusion cassette according to certain embodiments of the present disclosure.

FIGS. 8A-8J discloses alternate constructions of a matrix infusion cassette according to certain embodiments of the present disclosure. FIG. 8A illustrates an example matrix of locations of pumping actuators, indicated by the plus signs, and the valve actuators, indicated by the triangles, for an IV pump. The remaining FIGS. 8B-8J are examples of matrix infusion cassette configurations that may be compatible with this matrix of locations. Other configurations will be apparent to those of ordinary skill in the art.

Figure 8B:
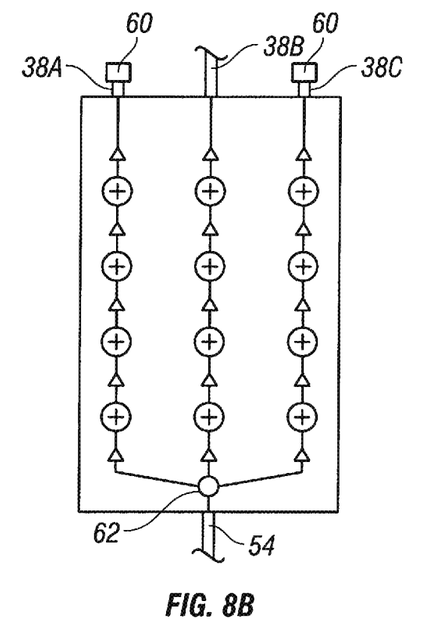

FIG. 8B illustrates a configuration having three inlet ports with IV set tubing bonded to the center inlet port 38B and the outlet port 54. Caps 60 are installed on the other two inlets 38A and 38C. Each inlet 38A-38C has a series of four pumping chambers analogous to the flow path illustrated in FIGS. 5A-5J with flow paths that terminate in a mixing chamber 62 and then flow to the outlet 54. This matrix infusion cassette may be utilized in a number of configurations. The IV set attached to inlet port 38B may be attached to a single fluid source (not shown) and the fluid pumped using only the chambers along the center flow path. Alternately, a second fluid source may be attached to either inlet port 38A or 38C and the flow rate of the second fluid controlled separately from the fluid source connected to inlet port 38B. In another alternate configuration, external "Y" connectors may be used to connect a single fluid source to two or more of inlets 38A-38C, utilizing more than one flow path and providing a higher maximum flow rate than can be provided by a single flow path.

Figure 8C:
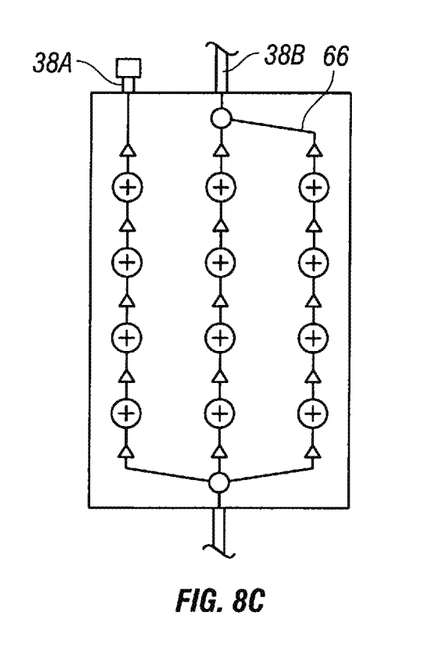

FIG. 8C illustrates an alternate configuration of the matrix infusion cassette wherein the inlet 38B is connected to a flow splitter 64 which feeds both the center and right flow paths. As the flow rate through each flow path is controlled by the pumping elements, there is no requirement for flow control in the flow splitter 64, which may be implemented as a simple chamber as shown. This configuration provides a maximum flow rate that is twice that of each inlet of the configuration shown in FIG. 8B. In FIG. 8C, the left flow path under inlet 38A remains available for connection of a second fluid source.

Figure 8D:
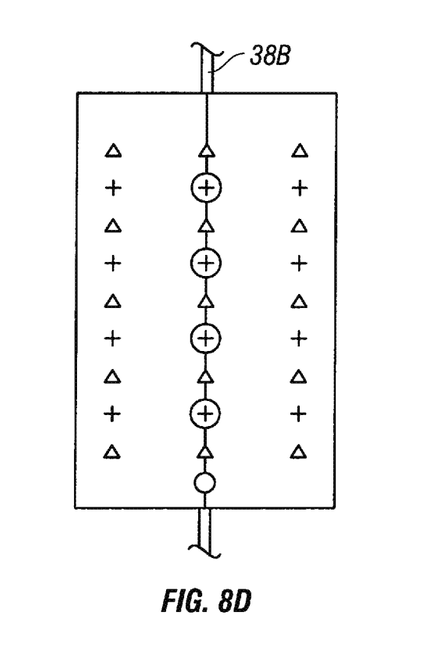

FIG. 8D is a basic configuration providing a single inlet 38B and a single flow path with a series of four pumping chambers. This matrix infusion cassette may have a lower cost than a fully populated matrix infusion cassette as disclosed in FIG. 8B while proving adequate pumping capacity for many treatments.

Figure 8E:
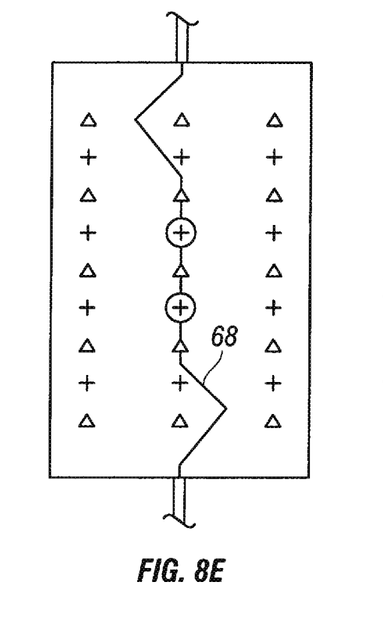

FIG. 8E is a minimal cost configuration having only two pumping chambers and three valves. The fluid conduits 68 have been routed around unused locations of valve actuators and pumping actuators to reduce the chance of erroneous operation.

Figure 8F:
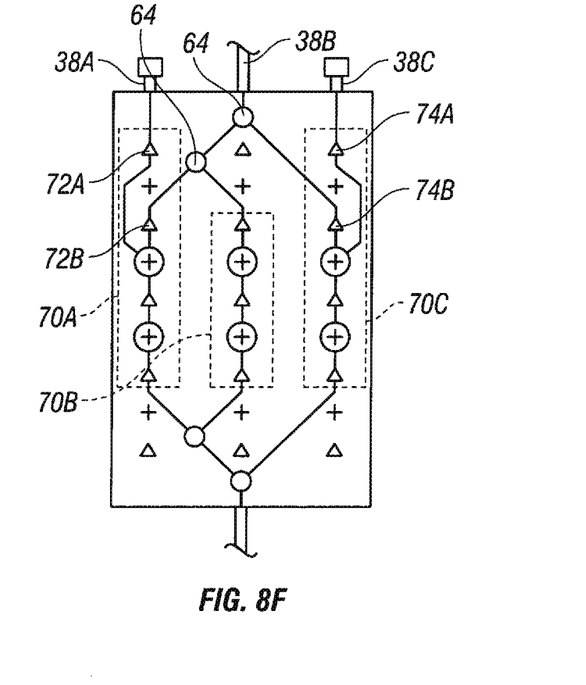

FIG. 8F is a configuration offering increased flexibility in configuration without external "Y" connectors. The pumping chambers are arranged in three parallel flow paths 70A, 70B, and 70C each having two pumping elements and three or four occluders. Flow path 70B is connected through flow splitters 64 to inlet 38B. Flow path 70A may be connected to inlet 38A or through flow splitters 64 to inlet 38B according to whether valves 72A or 72B are actuated. Similarly, flow path 70C may be connected to inlet 38C or through a flow splitter 64 to inlet 38B according to whether valves 74A or 74B are actuated. Through various combinations of actuation of valves 72A, 72B, 74A, and 74B, this system may be configured as a high flow system drawing fluid solely from inlet port 38B or as separately controlled flows of fluid from three separate fluids at inlet ports 38A, 38B, and 38C.

Figure 8G:
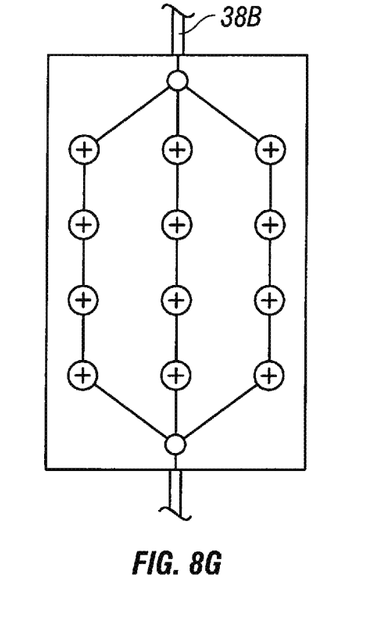

FIG. 8G illustrates an embodiment having a single inlet and three flow paths. This configuration offers a large dynamic range for administration of a single medical fluid, as two of the paths may be blocked during use.

Figure 8H:
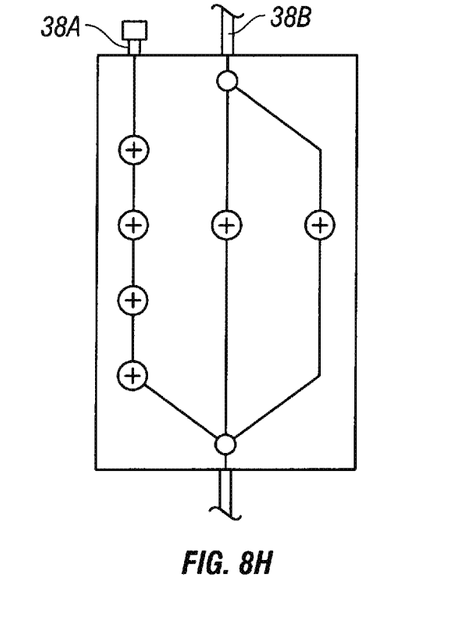

FIG. 8H discloses a configuration wherein inlet 38B has a pair of pumping chambers in parallel, enabling near continuous flow, while a second path from inlet 30A has multiple pumping chambers in series, enabling a higher rate flow for a second medical fluid.

There is no FIG. 8I.

Figure 8J:
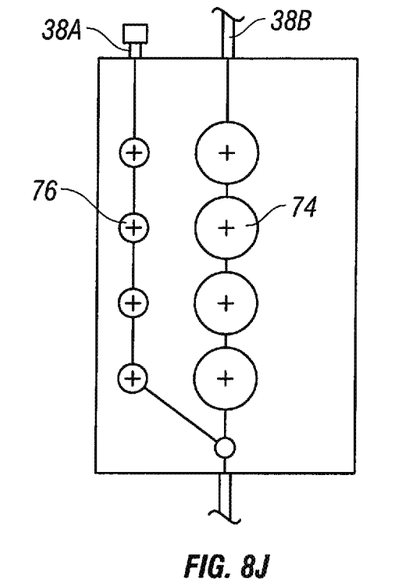

FIG. 8J illustrates an example configuration wherein the flow path under inlet 38B is configured with relatively large pumping chambers 74 to enable a high flow rate for one medical fluid and the flow path under inlet 38A is configured with relatively small pumping chambers 76 to enable precise administration of a second medical fluid using a low flow rate.

As can be seen from the variety of embodiments of FIGS. 8B-J, a variety of matrix infusion cassettes having a wide range of low rates and capabilities is possible for a single configuration of IV pump. The use of small pumping chambers, down to a few microliters in volume, allows precise control of a very low near-continuous flow rate. Pumping the full volume of a chamber is inherently more predictable than pumping a portion of a chamber, therefore pumping the full volume of a small chamber provides more accurate flow control that pumping a portion of a large chamber. At very low flow rates, where a microliter pumping volume could deliver near-continuous flow, an IV pump having a single large pumping chamber would only be able to achieve a comparable flow rate by periodically delivering a bolus of fluid produced by partially compressing the large chamber. In addition to the reduced accuracy of the partial compression of the large pumping chamber compared to the full compression of a small pumping chamber, true near-continuous delivery is preferable to intermittent delivery of a bolus of fluid that averages to the same delivery rate over time.

Matrix infusion cassettes may be provided as part of a disposable IV set, as shown in FIG. 1B, or as a separate disposable device connected with fittings to IV lines. Matrix infusion cassettes, especially embodiments of minimal complexity such as shown in FIGS. 8D-E, may add little if any cost to an IV set as the tubing of the IV set no longer comes into contact with the pump mechanism and therefore different materials may be used for the tubing.

Figure 9:
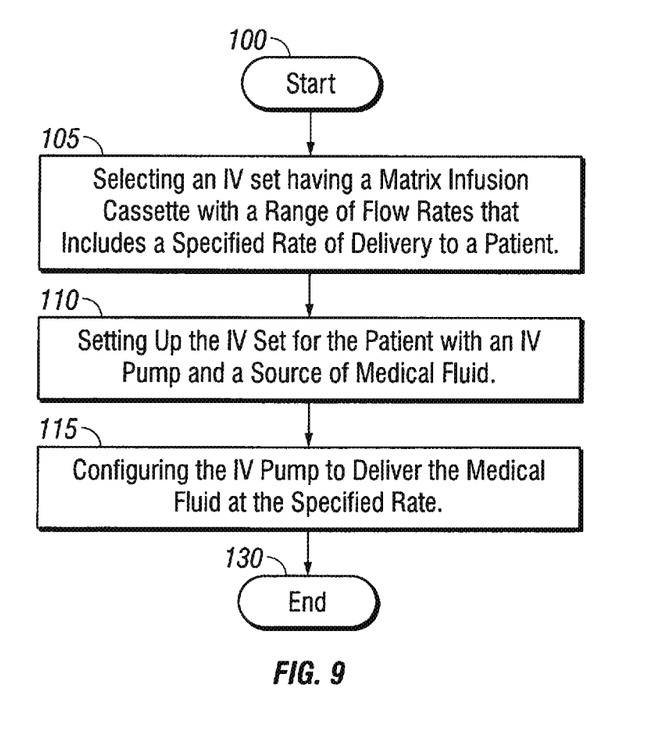
FIG. 9 is a flow chart disclosing an example process for using an IV set having a matrix infusion cassette according to certain embodiments of the present disclosure.

FIG. 9 is a flow chart disclosing an example process for using an IV set having a matrix infusion cassette according to certain embodiments of the present disclosure. Starting at 100, the first step 105 is to select an IV set having a range of flow rates that encompasses the administration rate specified in the physician's orders, or other source of instructions for treatment of the patient. The next step 110 is to set up the IV set for the patient, which includes connecting the IV set to the source of medical fluid, connecting the IV set to an IV pump, and inserting a catheter into a suitable vein or artery of the patient according to the standard and practices that are well known to nurses and other skilled healthcare workers. The next step 115 is to configure the IV pump to deliver the medical fluid through the IV set at the rate specified in the physician's orders. This ends the process as shown at step 130.

It can be seen that the disclosed embodiments of the matrix infusion cassette and an IV pump configured to actuate a matrix infusion cassette provide the ability to precisely control the delivery of one or more medical fluids over a wide range of flow rates. A matrix infusion cassette may have pumping chambers of various sizes configured in various flow paths. The matrix infusion cassette may have one or more inlets to enable the delivery of multiple medical fluids at independently controlled rates through a single IV set. The use of two parallel flow paths for a single fluid provides a near-continuous flow as the pumping chambers alternate in their delivery of fluid, compared to the intermittent delivery provided by some volumetric pumps.

The previous description is provided to enable any person skilled in the art to practice the various embodiments described herein. While the foregoing has described what are considered to be the best mode and/or other examples, it is understood that various modifications to these embodiments will be readily apparent to those skilled in the art, and the generic principles defined herein may be applied to other embodiments. Thus, the claims are not intended to be limited to the embodiments shown herein, but is to be accorded the full scope consistent with the language claims, wherein reference to an element in the singular is not intended to mean "one and only one" unless specifically so stated, but rather "one or more." Unless specifically stated otherwise, the terms "a set" and "some" refer to one or more. Pronouns in the masculine (e.g., his) include the feminine and neuter gender (e.g., her and its) and vice versa. Headings and subheadings, if any, are used for convenience only and do not limit the invention.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

A phrase such as an "aspect" does not imply that such aspect is essential to the subject technology or that such aspect applies to all configurations of the subject technology. A disclosure relating to an aspect may apply to all configurations, or one or more configurations. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. A phrase such an embodiment may refer to one or more embodiments and vice versa.

The word "exemplary" is used herein to mean "serving as an example or illustration." Any aspect or design described herein as "exemplary" is not necessarily to be construed as preferred or advantageous over other aspects or designs.

All structural and functional equivalents to the elements of the various embodiments described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. §112, sixth paragraph, unless the element is expressly recited using the phrase "means for" or, in the case of a method claim, the element is recited using the phrase "step for." Furthermore, to the extent that the term "include," "have," or the like is used in the description or the claims, such term is intended to be inclusive in a manner similar to the term "comprise" as "comprise" is interpreted when employed as a transitional word in a claim.

What is claimed is:

1. A matrix infusion cassette for use with an intravenous (IV) pump, the matrix infusion cassette comprising:
   a body configured to attach to the IV pump, the body having a plurality of inlet ports, an outlet port, and a plurality of pumping chambers arranged in a matrix having a plurality of parallel columns each having a first pumping chamber and a last pumping chamber; and
   a plurality of fluid conduits each connecting one of the plurality of inlet ports to the first pumping chamber of one of the plurality of columns, interconnecting the first and last pumping chambers in each column, and connecting the last pumping chamber of each of the plurality of columns to the outlet port; wherein each of the plurality of fluid conduits comprises a valve configured to selectable block flow through the respective fluid conduit.

2. The matrix infusion cassette of claim 1 wherein the pumping chambers each have a flexible wall.

3. The matrix infusion cassette of claim 2 wherein the flexible wall is configured such that displacement of the flexible wall of a respective pumping chamber individually actuates the respective pumping chamber.

4. The matrix infusion cassette of claim 1 further comprising a plurality of fluidic diodes located in the flow path of some of the fluid conduits.

5. The matrix infusion cassette of claim 1 wherein the fluid conduits interconnect two or more of the pumping chambers in series between at least one inlet port and the outlet port.

6. The matrix infusion cassette of claim 1 wherein the fluid conduits interconnect two or more of the pumping chambers in parallel between at least one inlet port and the outlet port.

7. The matrix infusion cassette of claim 6 wherein the fluid conduits interconnect a first set of the pumping chambers in series between a first inlet port and the outlet port and interconnect a second set of the pumping chambers in series between a second inlet port and the outlet port, wherein there are no interconnections between the first set and the second set of the pumping chambers except at the outlet port.

8. The matrix infusion cassette of claim 1 wherein the pumping chambers are a single common size.

9. The matrix infusion cassette of claim 1 wherein at least some of the pumping chambers are different sizes.

10. The matrix infusion cassette of claim 1 further comprising IV tubing attached to one or more of the inlet and outlet ports.

11. A matrix infusion pump comprising:
    a housing configured to attach to a matrix infusion cassette having a plurality of pumping chambers arranged in a first matrix having a plurality of parallel columns each having a first pumping chamber and a last pumping chamber, the cassette also having a plurality of valves;
    a plurality of pumping actuators attached to the housing and arranged such that each of the plurality of pumping actuators is configured to individually and separately actuate a respective one of the plurality of pumping chambers;
    a plurality of valve actuators attached to the housing and coupled to the processor, each of the plurality of valve actuators configured to actuate a respective one of the plurality of valves;
    a memory attached to the housing and configured to store instructions; and
    a processor attached to the housing and coupled to the memory and the pumping and valve actuators, the processor configured to retrieve the instructions from the memory and to cause the pumping and valve actuators to actuate the respective pumping chambers and valves according to the instructions.

12. The matrix infusion pump of claim 11 wherein the valve actuators are located in a second matrix of locations.

13. The matrix infusion pump of claim 11 wherein the valve actuators are individually and separately actuated.

14. A method comprising the steps of:
    connecting an IV set having a matrix infusion cassette to an intravenous (IV) pump, the cassette having a plurality of inlet ports, an outlet port, and a plurality of pumping chambers arranged in a matrix having a plurality of parallel columns each having a first pumping chamber and a last pumping chamber, the cassette also having a plurality of valves;
    respectively connecting the plurality of inlet ports to a plurality of sources of medical fluids; and
    configuring the matrix infusion pump to deliver each of the plurality of medical fluids at a respective flow rate.

* * * * *